(12) United States Patent
Mizuno et al.

(10) Patent No.: US 12,055,516 B2
(45) Date of Patent: Aug. 6, 2024

(54) SMELL DETECTION DEVICE AND SMELL DETECTION METHOD

(71) Applicant: HAMAMATSU PHOTONICS K.K., Hamamatsu (JP)

(72) Inventors: Seiichiro Mizuno, Hamamatsu (JP); Hiroo Yamamoto, Hamamatsu (JP); Sho Morita, Hamamatsu (JP); Toshiki Wakamori, Hamamatsu (JP)

(73) Assignee: HAMAMATSU PHOTONICS K.K., Hamamatsu (JP)

( * ) Notice: Subject to any disclaimer, the term of this patent is extended or adjusted under 35 U.S.C. 154(b) by 308 days.

(21) Appl. No.: 17/627,248

(22) PCT Filed: May 19, 2020

(86) PCT No.: PCT/JP2020/019797
§ 371 (c)(1),
(2) Date: Jan. 14, 2022

(87) PCT Pub. No.: WO2021/019870
PCT Pub. Date: Feb. 4, 2021

(65) Prior Publication Data
US 2022/0260519 A1  Aug. 18, 2022

(30) Foreign Application Priority Data

Jul. 26, 2019  (JP) .................. 2019-137872

(51) Int. Cl.
*G01N 27/414*  (2006.01)
*G01N 33/00*  (2006.01)

(52) U.S. Cl.
CPC ..... *G01N 27/4141* (2013.01); *G01N 33/0031* (2013.01)

(58) Field of Classification Search
CPC .. G01N 27/4148; G01N 27/414; G01N 27/00; G01N 27/16; G01N 33/0031;
(Continued)

(56) References Cited

U.S. PATENT DOCUMENTS

2003/0150252 A1* 8/2003 Wang ................... G01N 21/274
                                                        73/1.02
2013/0057251 A1  3/2013 Ahn et al.
(Continued)

FOREIGN PATENT DOCUMENTS

JP      S63-005255 A    1/1988
JP      2004-511799 A   4/2004
(Continued)

OTHER PUBLICATIONS

Duan, A high offset distribution tolerance high resolution ISFET array with auto-compensation for long-term bacterial metabolism monitoring, Mar. 2020 (Year: 2020).*
(Continued)

*Primary Examiner* — John Fitzgerald
*Assistant Examiner* — Truong D Phan
(74) *Attorney, Agent, or Firm* — Faegre Drinker Biddle & Reath LLP

(57) ABSTRACT

A smell detection device includes an ion sensor having a sensitive film and outputting an output signal in accordance with a potential change of the sensitive film, a substance adsorption film disposed on the sensitive film and changing its state by adsorbing a smell substance to be detected to cause the potential change of the sensitive film, and an adjuster acquiring the output signal of the ion sensor and adjusting a drive signal for driving the ion sensor to reduce an offset from a predetermined reference value in the output signal.

15 Claims, 11 Drawing Sheets

(58) Field of Classification Search
CPC .... G01N 27/126; G01N 27/227; G01N 30/00; G01N 2291/0256; G01N 2001/2826; G01N 1/405; G01N 2021/7723; G01N 27/225; G01N 2021/1772; G01N 2021/1774; G01N 2021/5957; G01N 2021/5961; G01N 2021/5965; G01N 23/2258; G01N 27/4141; G01N 27/333; G01N 27/4167; G01N 27/4165; H01L 21/82; H01L 29/762; H01L 2924/13073; H01L 2924/13072; H01L 27/14609; H01L 27/14641; B82Y 30/00

See application file for complete search history.

(56) References Cited

U.S. PATENT DOCUMENTS

| | | | |
|---|---|---|---|
| 2014/0139231 A1* | 5/2014 | Dasai | H01L 27/14609 324/438 |
| 2014/0200842 A1* | 7/2014 | Dasai | G01N 27/4165 702/104 |
| 2017/0241944 A1 | 8/2017 | Schneider et al. | |

FOREIGN PATENT DOCUMENTS

| | | |
|---|---|---|
| JP | 2010-122090 A | 6/2010 |
| JP | 2013-117469 A | 6/2013 |
| JP | 2016-080601 A | 5/2016 |
| JP | 2019-002820 A | 1/2019 |
| WO | WO-02/033397 A1 | 4/2002 |
| WO | WO-2005/090961 A1 | 9/2005 |
| WO | WO-2013/024791 A1 | 2/2013 |
| WO | WO-2018/211773 A1 | 11/2018 |
| WO | WO-2019/131564 A1 | 7/2019 |
| WO | WO-2019131564 A1 * | 7/2019 ............. G01N 27/00 |

OTHER PUBLICATIONS

International Preliminary Report on Patentability mailed Feb. 10, 2022 for PCT/JP2020/019797.

Shinmyo, Naoya et al., "Gas Distribution Imaging by Charge-Transfer-Type Sensor Arrays with Polyaniline Sensitive Layer," Proceedings of the 64th JSAP Spring Meeting, 2017, p. 11-330.

* cited by examiner

SMELL DETECTION DEVICE AND SMELL DETECTION METHOD

TECHNICAL FIELD

The present disclosure relates to a smell detection device and a smell detection method.

BACKGROUND ART

Patent Document 1 discloses that voltage offset compensation is performed in a detection circuit with respect to an output signal of a semiconductor biosensor. Patent Document 2 discloses that current offset compensation is performed in a detection circuit with respect to an output signal of a sensor for detecting DNA.

CITATION LIST

Patent Document

[Patent Document 1] Japanese Unexamined Patent Application Publication No. 63-5255
[Patent Document 2] Japanese Unexamined Patent Application Publication (Translation of PCT Application) No. 2004-511799

SUMMARY OF INVENTION

Technical Problem

The offset compensation method described in Patent Documents 1 and 2 corrects an output signal from a sensor. That is, in the above method, after an output signal including an offset component is obtained, correction processing for removing the offset component is performed ex post facto. In such a method, there is a problem that the dynamic range of the output is reduced due to the offset component included in the output signal.

An object of one aspect of the present disclosure is to provide a smell detection device and a smell detection method capable of effectively suppressing a decrease in dynamic range.

Solution to Problem

A smell detection device according to an aspect of the present disclosure includes: an ion sensor having an ion sensitive portion and configured to output an output signal in accordance with a potential change of the ion sensitive portion; a substance adsorption film disposed on the ion sensitive portion and configured to change a state of the substance absorption film by adsorbing a smell substance to be detected and to cause the potential change of the ion sensitive portion; and an adjuster configured to acquire the output signal of the ion sensor and adjust a drive signal for driving the ion sensor to reduce an offset from a predetermined reference value in the output signal.

The smell detection device includes an adjuster configured to adjust a drive signal for driving the ion sensor to reduce an offset of an output signal of the ion sensor. Therefore, for example, in a state where the potential of the ion sensitive portion is not changed (that is, in a state where the smell substance is not adsorbed to the substance adsorption film), the offset component of the output signal of the ion sensor can be reduced by adjusting the drive signal by the adjuster. The offset component of the output signal can be suppressed by adjusting the drive signal, which is an input signal to the ion sensor. Therefore, according to the smell detection device, it is possible to effectively suppress a decrease in the dynamic range due to the offset component of the output signal.

The adjuster may be configured to be able to switch between a first operation mode in which the drive signal is adjusted based on the output signal and a second operation mode in which the drive signal adjusted in the first operation mode is maintained. According to the above configuration, it is possible to appropriately switch between the first operation mode for adjusting the drive signal and the second operation mode for performing smell detection using the adjusted drive signal according to the situation.

The smell detection device may further include an electrode configured to apply a reference voltage to the substance adsorption film, and the drive signal may be the reference voltage. According to the above configuration, the offset component of the output signal can be suitably suppressed by adjusting the reference voltage applied to the substance adsorption film.

The ion sensor may include an ID portion configured to store an electric charge to be injected into a potential well whose depth changes in accordance with the potential change of the ion sensitive portion, and an ICG portion configured to control an amount of the electric charge injected from the ID portion to the potential well. The ion sensor may be configured to inject the electric charge from the ID portion into the potential well by changing a potential of the ICG portion while keeping a potential of the ID portion constant, and the drive signal may be a voltage applied to the ID portion. According to the above configuration, in the ion sensor configured to inject the electric charge into the potential well by changing the potential of the ICG portion while keeping the potential of the ID portion constant, the offset component of the output signal can be suitably suppressed by adjusting the voltage of the ID portion that determines an injection amount of the electric charge.

The ion sensor may include an ID portion configured to store an electric charge to be injected into a potential well whose depth changes in accordance with the potential change of the ion sensitive portion, and an ICG portion configured to control an amount of the electric charge injected from the ID portion to the potential well. The ion sensor may be configured to inject the electric charge from the ID portion into the potential well by changing a potential of the ID portion while keeping a potential of the ICG electrode constant, and the drive signal may be a voltage applied to the ICG portion. According to the above configuration, in the ion sensor configured to inject the electric charge into the potential well by changing the potential of the ID portion while keeping the potential of the ICG portion constant, the offset component of the output signal can be suitably suppressed by adjusting the voltage of the ICG portion that determines a so-called leveling height of the electric charge.

The adjuster may include a first adjuster configured to receive the output signal and output a signal adjusted in a direction opposite to an offset direction of the output signal, and a second adjuster configured to generate the drive signal by adjusting a gain of the signal output by the first adjuster. According to the above configuration, it is possible to obtain the drive signal which is adjusted in the direction of reducing the offset of the output signal by the first adjuster and is adjusted to an appropriate magnitude by the second adjuster.

The ion sensor may include a plurality of pixel groups. Each pixel group of the plurality of pixel groups may include one or more pixels each having the ion sensitive portion independently. The adjuster may be provided for the each pixel group. The adjuster provided in one pixel group may be configured to adjust the drive signal common to each pixel included in the one pixel group based on the output signal of the each pixel included in the one pixel group. According to the above configuration, it is possible to individually adjust the drive signal in accordance with the characteristics of each pixel group, compared to a case where the drive signal is collectively adjusted for all the pixels included in the ion sensor.

The substance adsorption film may be provided for the each pixel group. According to the above configuration, the drive signal can be appropriately adjusted in accordance with the characteristics of each substance adsorption film.

According to an aspect of the present disclosure, there is provided a smell detection method by a smell detection device including: an ion sensor having an ion sensitive portion and configured to output an output signal in accordance with a potential change of the ion sensitive portion; and a substance adsorption film disposed on the ion sensitive portion and configured to change a state of the substance absorption film by adsorbing a smell substance to be detected and to cause the potential change of the ion sensitive portion. The smell detection method includes: a first step of acquiring an output signal of the ion sensor and adjusting a drive signal for driving the ion sensor such that an offset from a predetermined reference value in the output signal is reduced, in a state where the smell detection device is disposed in an atmosphere in which the smell substance to be detected does not exist; a second step of introducing an air to be inspected into the smell detection device while maintaining the drive signal adjusted in the first step; and a third step of detecting the smell substance based on the output signal of the ion sensor obtained after the second step.

According to the smell detection method, it is possible to appropriately adjust the drive signal in an atmosphere in which the smell substance is not present (that is, in an environment in which the output signal of the ion sensor ideally coincides with the reference value). Then, by performing smell detection using the adjusted drive signal, the offset component of the output signal can be suppressed. Therefore, according to the smell detection method, it is possible to effectively suppress a decrease in the dynamic range caused by the offset component of the output signal.

In the smell detection method, the processing of the first step may be executed again after a predetermined period has elapsed since the processing of the second step was executed. Once the drive signal is adjusted, the offset component of the output signal of the ion sensor gradually increases over time due to changes over time in the environment (e.g., temperature, humidity, etc.) around the ion sensor. According to the above configuration, by periodically adjusting the drive signal, it is possible to continuously perform smell detection in a state in which the offset component of the output signal is suppressed to a predetermined value or less.

Advantageous Effects of Invention

According to an aspect of the present disclosure, a smell detection device and a smell detection method capable of effectively suppressing a decrease in dynamic range may be provided.

DESCRIPTION OF EMBODIMENTS

Figure 1:
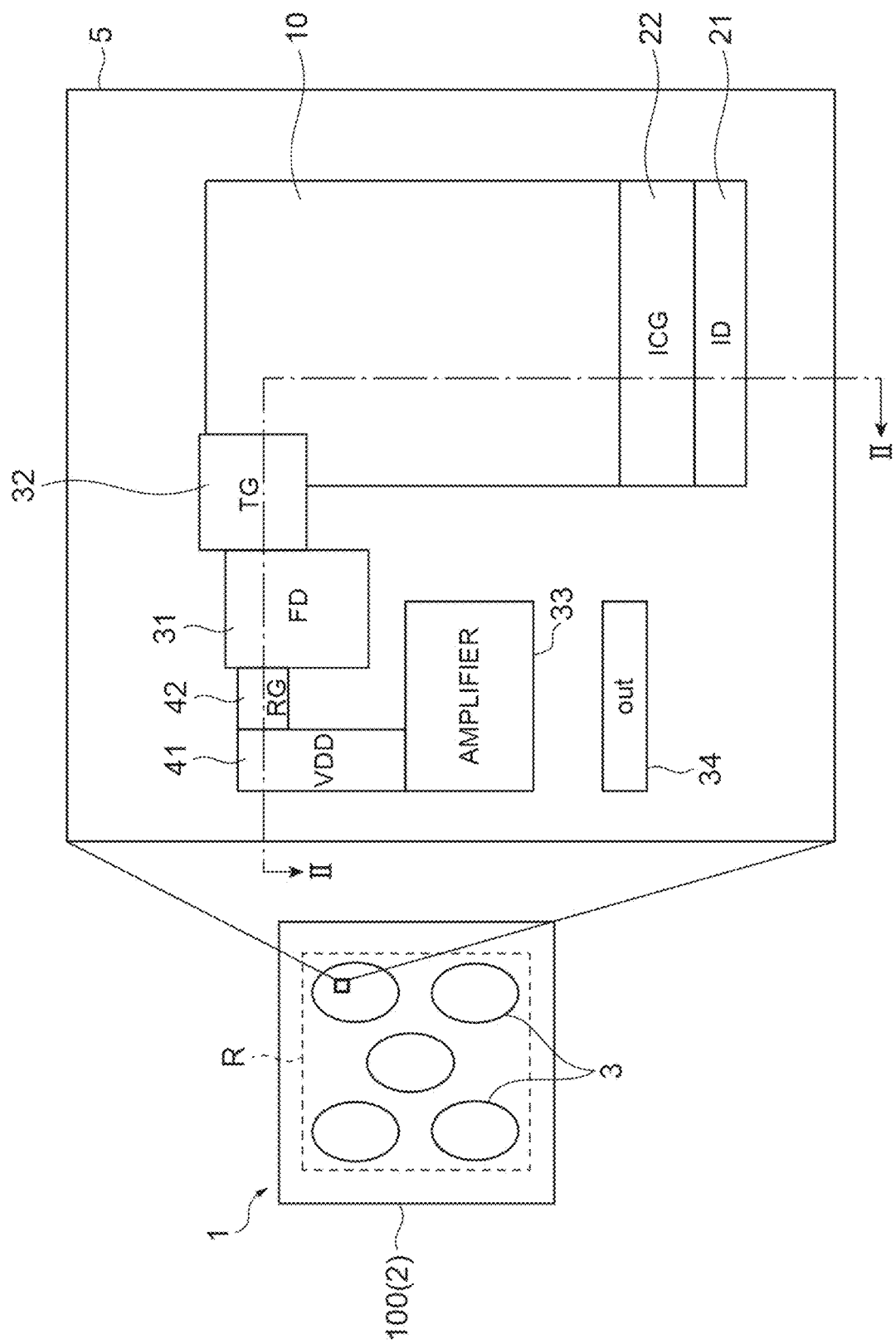
FIG. 1 is a schematic plan view of the smell detection device of the first embodiment.

Hereinafter, embodiments of the present disclosure will be described in detail with reference to the accompanying drawings. In the description of the drawings, the same reference numerals are used for the same or equivalent element, and redundant description is omitted.

First Embodiment

Figure 2:
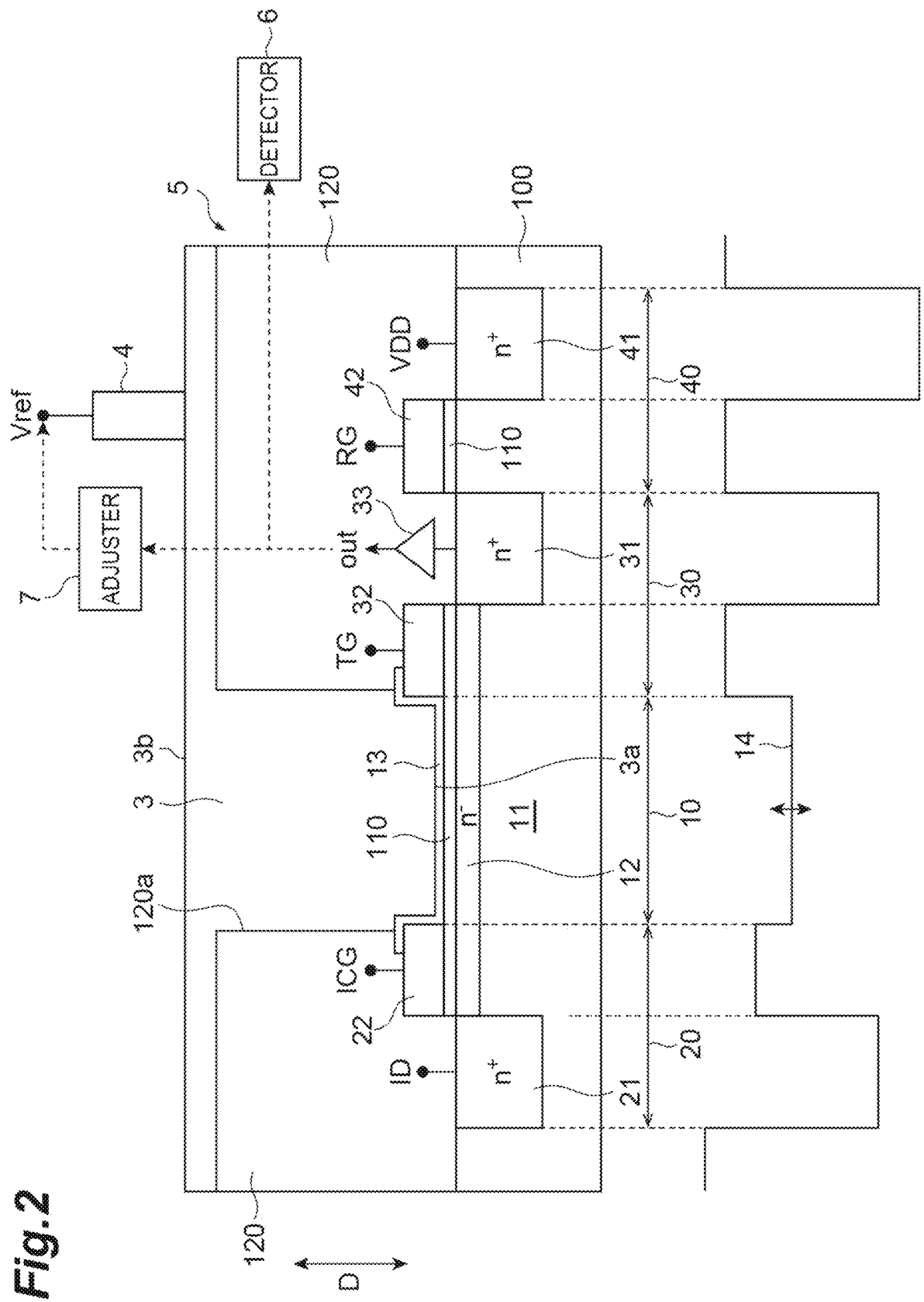
FIG. 2 is a diagram schematically showing a cross-sectional configuration of a detection unit.

FIG. 1 is a schematic plan view of the smell detection device 1 of the first embodiment. The right part of FIG. 1 schematically shows a layout example common to the respective detection units 5. FIG. 2 schematically shows a cross-sectional configuration of the detection unit 5 taken along line II-II in FIG. 1. The smell detection device 1 includes an ion sensor 2, a substance adsorption film 3 provided on the ion sensor 2, an electrode 4, a detector 6, and an adjuster 7.

The ion sensor 2 is a sensor in which a plurality of detection units 5 arranged two-dimensionally are formed on a substrate 100. The ion sensor 2 is a so-called charge transfer type CMOS image sensor. The plurality of detection units 5 are two-dimensionally arranged in M rows and N columns (for example, 256 rows and 256 columns) in a pixel formation region R provided on a chip of the ion sensor 2 (in the present embodiment, a rectangular region provided in a center of the chip), thereby forming a pixel array. M and N are each an integer of two or more. One detection unit 5 corresponds to one detection unit (pixel). The size (pixel size) of one detection unit 5 is, for example, 30 µm×30 µm.

Each substance adsorption film 3 is disposed (formed) so as to extend over a plurality of detection units 5 in the pixel formation region R. The substance adsorption film 3 is a thin film that changes its state (for example, electrical characteristics) by adsorbing a smell substance to be detected. The smell substance to be detected by the substance adsorption film 3 (i.e., the smell substance detectable by the substance adsorption film 3) varies depending on the material and composition of the substance adsorption film 3. Here, the "smell" is something that stimulates the sense of smell of an organism such as a human being or an animal, and the "smell substance" is a chemical substance (for example, a substance in which a specific single molecule or a specific group of molecules are assembled at a predetermined concentration) that causes the smell. As the substance adsorption film 3, for example, a polyaniline sensitive film or the like having sensitivity to ammonia or the like can be used. Among the detection units 5 arranged in the pixel formation region R, the detection unit 5 provided with the substance adsorption film 3 functions as a unit detection element capable of detecting the smell. The substance adsorption film 3 may be provided in the entire pixel formation region R (i.e., all the detection units 5 arranged in the pixel formation region R), or there may be a detection unit 5 in which the substance adsorption film 3 is not provided.

As shown in FIG. 1, in this embodiment, a plurality of (here, five) substance adsorption films 3 separated from each other are provided on one chip. The plurality of substance adsorption films 3 provided on the one ion sensor 2 may be a plurality of substance adsorption films having mutually different component amounts (contents) of the same material (for example, polyaniline) or may be a plurality of substance adsorption films formed of mutually different materials. By using a plurality of substance adsorption films 3 having different component amounts or materials, it is possible to detect various smell substances based on a combination of measurement results of the respective substance adsorption films 3. For example, when table information (smell database) in which a combination of measurement results of a plurality of substance adsorption films is associated with a specific smell substance is prepared in advance, the smell substance corresponding to the combination of measurement results of each of the plurality of substance adsorption films 3 can be estimated by referring to the table information.

As shown in FIGS. 1 and 2, each detection unit 5 is formed on one main surface side of the substrate 100. The substrate 100 is a semiconductor substrate of a first conductivity type (for example, n-type) formed of, for example, silicon. In each detection unit 5, an injection diode portion 21 (hereinafter referred to as "ID portion 21"), a floating diffusion portion 31 (hereinafter referred to as "FD portion 31"), and a reset drain portion 41 (hereinafter referred to as "RD portion 41"), which are each a first conductive type region, are formed along the main surface of the substrate 100. A diffusion layer 11 of the second conductivity type (for example, p-type) is formed between the ID portion 21 and the FD portion 31 of the substrate 100. A first conductive type region 12 doped in a first conductive type is formed on a surface of the diffusion layer 11.

An input control gate electrode 22 (hereinafter referred to as "ICG portion 22"), a transfer gate electrode 32 (hereinafter referred to as "TG portion 32"), and a reset gate electrode 42 (hereinafter referred to as "RG portion 42") are formed on the main surface of the substrate 100 via an insulating protective film 110. As the protective film 110, for example, $SiO_2$ or the like can be used. On the main surface of the substrate 100, an amplifier (signal amplifier) 33 that amplifies an out signal corresponding to the electric charge amount accumulated in the FD portion 31 and an output circuit 34 that is a source follower circuit that outputs the out signal amplified by the amplifier 33 are provided.

A sensitive film 13 (ion sensitive portion) is provided in a region between the ICG portion 22 and the TG portion 32 via a protective film 110. The sensitive film 13 is an ion sensitive film having a property of changing a potential (membrane potential) in accordance with a state of the substance adsorption film 3 disposed on the sensitive film 13. For example, $Si_3N_4$ or the like may be used as the sensitive film 13. In the present embodiment, the sensitive film 13 is formed continuously from the ICG portion 22 to the TG portion 32 so as to cover a part of the ICG portion 22 and the TG portion 32 so that the ICG portion 22 and the TG portion 32 do not come into contact with the substance adsorption film 3. However, the sensitive film 13 may be provided only between the ICG portion 22 and the TG portion 32, or may be formed so as not to cover a part of the ICG portion 22 and the TG portion 32. That is, the sensitive film 13 may be formed only on the protective film 110 between the ICG portion 22 and the TG portion 32.

An insulating passivation layer 120 is formed on the main surface of the substrate 100 so as to cover these members provided on the main surface of the substrate 100. For example, $Si_3N_4$ may be used as the passivation layer 120. The substance adsorption film 3 is provided so as to cover the passivation layer 120. An opening 120a for exposing the upper surface of the sensitive film 13 to the outside is formed in the passivation layer 120. The sensitive film 13 is in contact with the substance adsorption film 3 through the opening 120a. That is, a part of the substance adsorption film 3 enters the inside of the opening 120a. Inside the opening 120a, an inner surface 3a of the substance adsorption film 3 on the substrate 100 side is in contact with the sensitive film 13.

The electrode 4 applies a reference voltage Vref to the substance adsorption film 3. The shape, arrangement, and the like of the electrode 4 are not limited to a specific form. For example, the electrode 4 may be a built-in electrode (for example, a metal wiring formed by a CMOS process) disposed inside the substance adsorption film 3. Alternatively, the electrode 4 may be an external electrode (for example, a membrane electrode formed by a MEMS process) disposed along the outer surface 3b (surface opposite to the inner surface 3a) of the substance adsorption film 3. The electrode 4 may be formed of a material capable of being in contact with the substance absorption film 3 and applying a voltage to the substance adsorption film 3. As the electrode 4, for example, Al—Si—Cu or the like can be used.

The detector 6 monitors an out signal which is an output signal of the ion sensor 2 in accordance with the potential of the sensitive film 13. Then, the detector 6 detects the smell substance by detecting a change in the out signal corresponding to the potential change of the sensitive film 13. Specifically, by continuously applying a constant reference voltage Vref to the substance adsorption film 3, the smell substance can be detected as follows. When the potential change of the sensitive film 13 does not occur (that is, when the smell substance is not adsorbed to the substance adsorption film 3), the out signal (voltage value) becomes a standard voltage (reference value) corresponding to the reference voltage Vref. Therefore, the detector 6 can determine that the smell substance is not detected while the standard voltage is output as the out signal. On the other hand, when the smell substance is adsorbed to the substance adsorption film 3 and the potential of the sensitive film 13 changes in accordance with the change in the state of the substance adsorption film 3, the out signal changes in accordance with the potential change. Therefore, the detector 6 can detect the smell substance (that is, the fact that the smell substance is adsorbed to the substance adsorption film 3) based on the difference (change amount) between the out signal and the standard voltage. For example, the detector 6 can detect the smell substance by detecting that the change amount exceeds a predetermined threshold. The detector 6 may detect a change from a state with a smell (a state in which the smell substance is adsorbed to the substance adsorption film 3) to a state without a smell based on the potential change. Further, the detector 6 may estimate the smell substance based on the pattern (for example, speed) of the potential change. The detector 6 may be configured as, for example, a computer device including a processor, a memory, a storage, a communication device, and the like.

Next, the functional configuration and operation principle of the detection unit 5 will be described. The detection unit 5 includes a sensing section 10, a supply section 20, a movement/accumulation section 30, and a removal section 40. In the present embodiment, the electric charge is an electron.

The sensing section 10 is a region where the sensitive film 13 is exposed to the outside (i.e., to the substance adsorption film 3) through the opening 120a of the passivation layer 120. More specifically, the sensing section 10 is a region where the sensitive film 13 faces the first conductive type region 12 via the protective film 110 between the ICG portion 22 and the TG portion 32. That is, the sensing section 10 is a sensing region formed by stacking the diffusion layer 11, the first conductive type region 12, the protective film 110, and the sensitive film 13. When the substance adsorption film 3 adsorbs the smell substance to be detected, the state (for example, ion concentration) of the substance adsorption film 3 changes. In the sensitive film 13, a potential change corresponding to the change in the state of the substance adsorption film 3 occurs. The depth of the potential well 14 of the diffusion layer 11 facing the sensitive film 13 changes in accordance with the potential change of the sensitive film 13.

The supply section 20 includes the ID portion 21 and the ICG portion 22. The ID portion 21 is a portion for storing an electric charge to be injected into the potential well 14. The ICG portion 22 is a part for controlling the amount of the electric charges injected from the ID portion 21 to the potential well 14.

The movement/accumulation section 30 includes the TG portion 32 and the FD portion 31. The TG portion 32 is a portion for transferring the electric charge from the potential well 14 to the FD portion 31. The FD portion 31 is a portion for accumulating the electric charge transferred from the potential well 14. Specifically, by changing the voltage of the TG portion 32, the potential of a region (hereinafter referred to as "TG region") facing the TG portion 32 in the substrate 100 is changed, and the electric charge filled in the potential well 14 can be transferred and accumulated in the FD portion 31.

The removal section 40 includes the RG portion 42 and the RD portion 41. The removal section 40 is a section for resetting (removing) the electric charge accumulated in the FD portion 31. Specifically, the electric charge accumulated in the FD portion 31 can be discharged to the RD portion 41 (VDD) by changing the voltage of the RG portion 42 to change the potential of a region (hereinafter, referred to as an "RG region") facing the RG portion 42 in the substrate 100.

Figure 3:
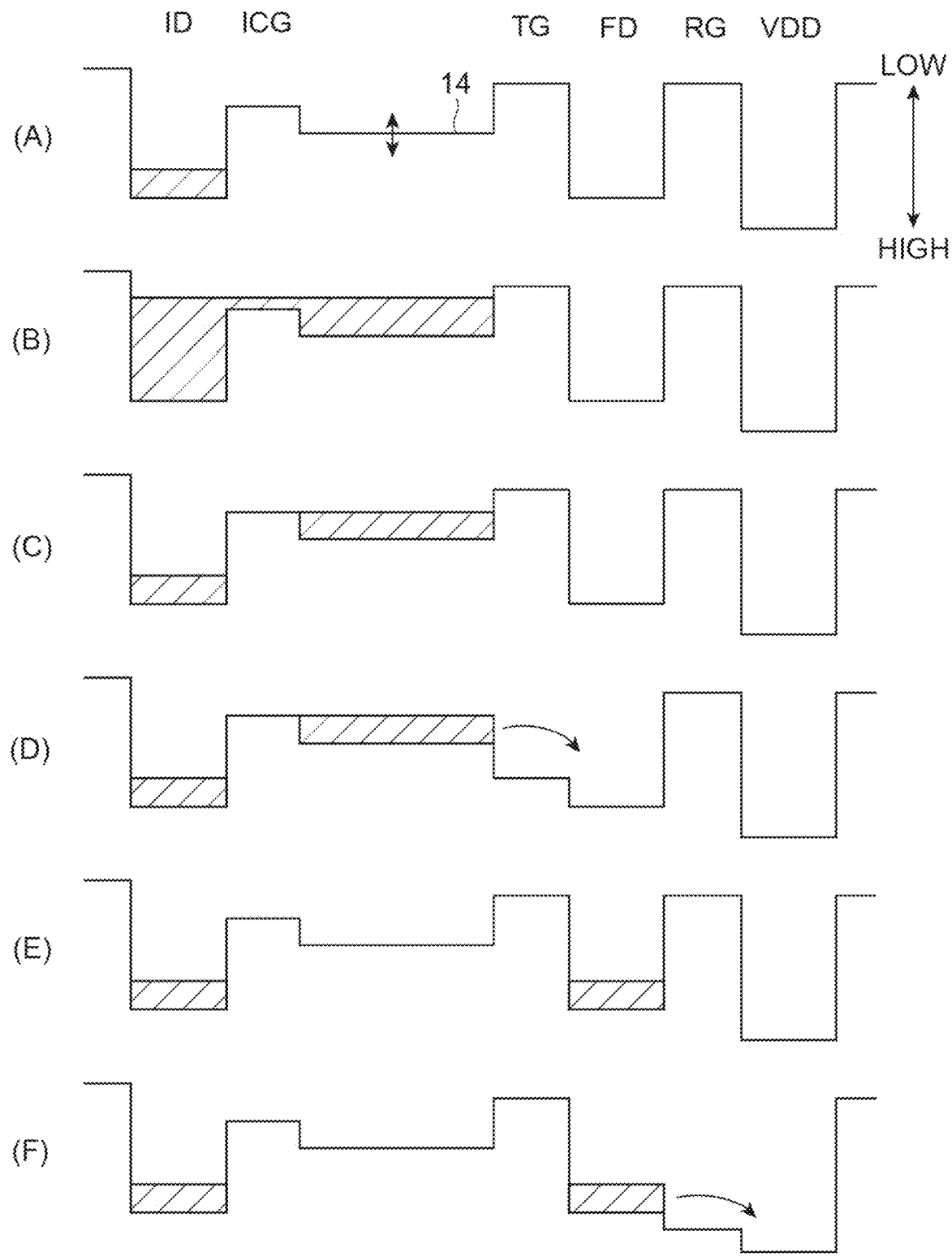
FIG. 3 is a diagram illustrating an example of the operation of the detection unit by the ID driving system.
Figure 4:
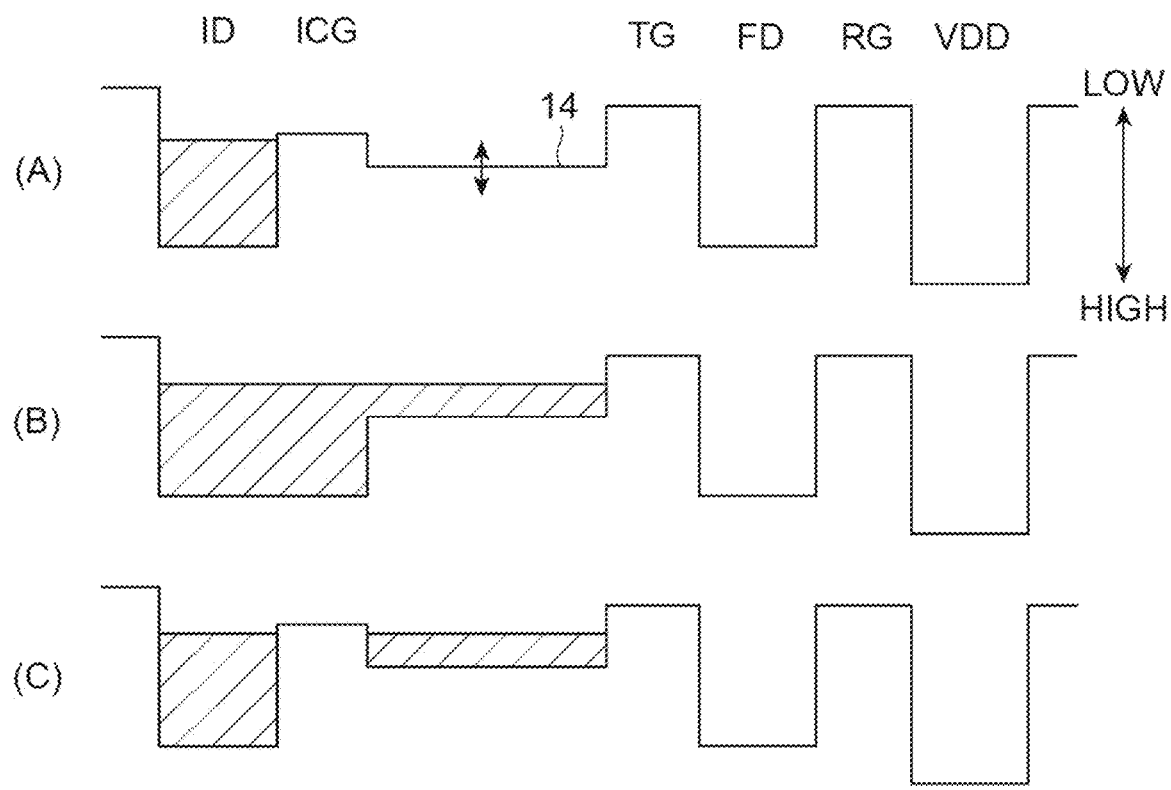
FIG. 4 is a diagram illustrating an example of the operation of the detection unit by the ICG driving system.

Next, an operation example of the detection unit 5 will be described. FIG. 3 shows an operation example of a method of injecting an electric charge from the ID portion 21 into the potential well 14 by changing the potential of the ID portion 21 in a state where the potential of the ICG portion 22 is constant (hereinafter referred to as "ID driving system"). FIG. 4 shows an operation example of a method of injecting an electric charge from the ID portion 21 into the potential well by changing the potential of the ICG portion 22 in a state where the potential of the ID portion 21 is constant (hereinafter referred to as "ICG driving system").

(ID Driving System)

The ID driving system will be described with reference to FIG. 3. First, as shown in (A) of FIG. 3, when the substance adsorption film 3 adsorbs a smell substance and a change in state of the substance adsorption film 3 occurs, a potential change occurs in the sensitive film 13 located immediately below the substance adsorption film 3, and the depth of the potential well 14 changes in accordance with the potential change. Subsequently, as shown in (B) of FIG. 3, the electric charge is accumulated in the ID portion 21 by lowering the potential of the ID portion 21. The electric charge accumulated in the ID portion 21 is injected into the potential well 14 beyond a region (hereinafter, referred to as an "ICG region") facing the ICG portion 22 in the substrate 100. At this time, the potential of the TG region is controlled to be lower than the potential of the ID portion 21. Therefore, the electric charge injected into the potential well 14 does not reach the FD portion 31 beyond the TG region.

Subsequently, as shown in (C) of FIG. 3, the electric charge is extracted from the ID portion 21 by restoring (raising) the potential of the ID portion 21. As a result, an electric charge scraped off at a predetermined potential level of the ICG region remains in the potential well 14. The electric charge amount left in the potential well 14 corresponds to the depth of the potential well 14.

Subsequently, as shown in (D) of FIG. 3, the voltage of the TG portion 32 is raised, whereby the electric charge remaining in the potential well 14 is transferred to the FD portion 31. Thereafter, the voltage of the TG portion 32 is returned to the original voltage, and the state shown in (E) of FIG. 3 is obtained. In this state, an out signal corresponding to the electric charge amount accumulated in the FD portion 31 is output to the detector 6 via the amplifier 33 and the output circuit 34. Accordingly, in the detector 6, the smell detected in the substance adsorption film 3 (that is, the smell substance adsorbed by the substance adsorption film 3) is detected based on the amount of change of the out signal from the standard voltage. Subsequently, as shown in (F) of FIG. 3, the voltage of the RG portion 42 is raised, whereby the electric charge accumulated in the FD portion 31 is discharged to the RD portion 41. RD portion 41 is connected to the VDD power supply. As a result, the negatively charged electric charge is absorbed in the RD portion 41.

The above-described operations of (B) to (E) of FIG. 3 may be repeated a plurality of times. As a result, the electric charge amount accumulated in the FD portion 31 can be increased, and the out signal can be amplified by the number of repetitions. Further, the amplifier 33 may be omitted by amplifying the out signal by such a repetitive operation. By executing the operation (accumulation operation) of repeating (B) to (E) of FIG. 3, the resolution can be improved. The above-described accumulation operation is particularly effective in a smell sensor in which an instantaneous state change is unlikely to occur, such as the smell detection device 1. In addition, according to the ion sensor 2 which is a CMOS image sensor, since it is possible to perform reading at a higher speed than that of the ISFET type ion sensor 2A of the fourth embodiment described later, it is possible to preferably perform smell detection even when the accumulation operation is performed. When the cumulative number of times (the number of times of repetition) is set to N times, gain becomes N times. However, for example, gain may be adjusted to 1/N times by a gain adjuster 72 described later, or a ratio of capacitors C1 and C2 included in a feedback circuit 71 described later may be adjusted.

(ICG Driving System)

Next, the ICG driving system will be described with reference to FIG. 4. In the ICG driving system, the operations of (A) to (C) of FIG. 3 are replaced with the operations of (A) to (C) of FIG. 4. First, as shown in (A) of FIG. 4, the potential of the ID portion 21 is set to a constant value lower than the potential of the potential well 14 and higher than the potential of the TG region. On the other hand, the potential of the ICG region is made lower than the potential of the ID portion 21. Subsequently, as shown in (B) of FIG. 4, the electric charge is supplied from the ID portion 21 to the potential well 14 by making the potential of the ICG region higher than the potential of the potential well 14. Subsequently, as shown in (C) of FIG. 4, the potential of the ICG region is set to be lower than the potential of the ID portion 21 again, so that electric charges up to the preset potential of the ID portion 21 remain in the potential well 14. As a result, the electric charges having a potential equivalent to that of the ID portion 21 are accumulated in the potential well 14. Subsequent operations in the ICG driving system are the same as the operations in (D) to (F) of FIG. 3.

Next, the adjuster 7 will be described. The adjuster 7 adjusts a drive signal for driving the ion sensor 2. Here, the drive signal is an input signal necessary for operating the detection unit 5 to perform measurement of the out signal (smell measurement) as described above. In the present embodiment, the drive signal is a reference voltage Vref applied to the substance adsorption film 3 by the electrode 4. The adjuster 7 may be provided in each pixel (detection unit 5) in the CMOS chip of the ion sensor 2, or may be provided in units of rows, columns, or specific areas. The adjuster 7 may be provided on a control substrate (not shown) or the like outside the CMOS chip. In this case, a signal processing circuit or the like may be provided between the adjuster 7 and the electrode 4. When a single adjuster 7 is used as the adjuster 7 common to a plurality of pixels, a pixel selection circuit, a buffer amplifier, and the like may be provided between the output circuit 34 of each pixel and the adjuster 7.

First, the reason why the drive signal needs to be adjusted by the adjuster 7 will be described. As described above, the detector 6 detects the smell substance based on the difference between the out signal and the predetermined standard voltage. That is, the detector 6 detects the smell substance based on the characteristic that the out signal in a state where the smell substance is not absorbed to the substance absorption film 3 (hereinafter referred to as a "standard state") substantially coincides with the standard voltage, and that the out signal in a state where the smell substance is absorbed to the substance absorption film 3 is relatively largely deviated from the standard voltage. Therefore, in order to detect the smell substance appropriately and with high accuracy, the precondition that the out signal in the standard state substantially coincides with the standard voltage must be satisfied. However, in practice, when the measurement by the smell detection device 1 is continued for a long period (for example, several hours or more), an output drift may occur due to a temporal change in the environment (for example, temperature, humidity, and the like) around the ion sensor 2. Due to the influence of such an output drift, the out signal in the standard state may gradually deviate greatly from the predetermined standard voltage. Therefore, the adjuster 7 adjusts the drive signal (reference voltage Vref in the present embodiment) so that the difference (offset) between the out signal and the standard voltage in the standard state decreases (ideally, the offset becomes 0).

Figure 5:
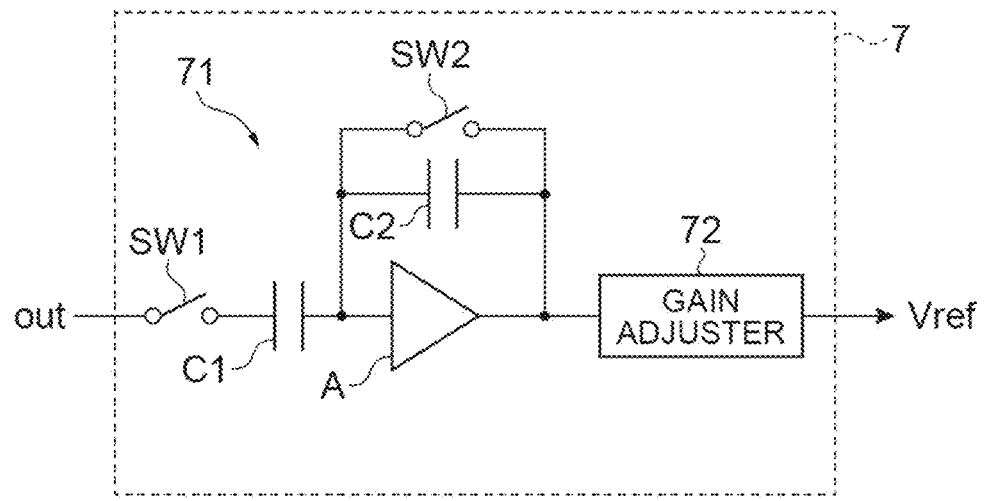
FIG. 5 is a diagram illustrating an example of the configuration of an adjuster.

FIG. 5 is a diagram illustrating a configuration example of the adjuster 7. The adjuster 7 includes a feedback circuit 71 (first adjuster) and a gain adjuster 72 (second adjuster). The feedback circuit 71 receives the out signal and outputs a signal adjusted in a direction opposite to the offset direction of the out signal to the gain adjuster 72. In the present embodiment, as an example, the feedback circuit 71 is configured to output a signal adjusted by the same magnitude as the offset of the out signal in a direction opposite to the offset direction of the out signal.

The feedback circuit 71 is a circuit in which a switch SW1, a capacitor C1, and an integration circuit (an amplifier A, a capacitor C2, and a switch SW2) are connected in series in this order from the input side of the out signal. The capacitor C2 and the switch SW2 are connected in parallel to each other and directed between the input end and the output end of the amplifier A. When the switch SW2 is in the on state, the charge accumulation of the capacitor C2 is initialized, and the feedback circuit 71 outputs a voltage value corresponding to the input voltage of the amplifier A. On the other hand, when the switch SW2 is in the off state, the capacitor C2 accumulates electric charge, and the feedback circuit 71 outputs a voltage value corresponding to the charge accumulation amount in the capacitor C2. According to the feedback circuit 71, a signal adjusted in a direction opposite to the offset direction of the out signal can be output by turning on the switch SW1, and the adjusted signal can be output while being maintained by turning off the switch SW2.

The gain adjuster 72 generates a drive signal by adjusting the gain of the signal output by the feedback circuit 71. The drive signal output from the gain adjuster 72 is input to the electrode 4. Here, the relationship between the out signal and the drive signal is not necessarily one to one (1:1). That is, the out signal does not necessarily rise (or fall) by the same amount that the drive signal (voltage) is raised (or lowered). For example, there may be a case where it is necessary to increase the drive signal by "v1×a" in order to increase the out signal by "v1". The gain adjuster 72 adjusts the signal output from the feedback circuit 71 in accordance with the relationship between the out signal and the drive signal grasped in advance, thereby obtaining a final drive signal. The gain adjuster 72 may be omitted when the signal output from the feedback circuit 71 can be used as the drive signal as it is, such as when the relationship between the out signal and the drive signal is one to one.

Figure 6:
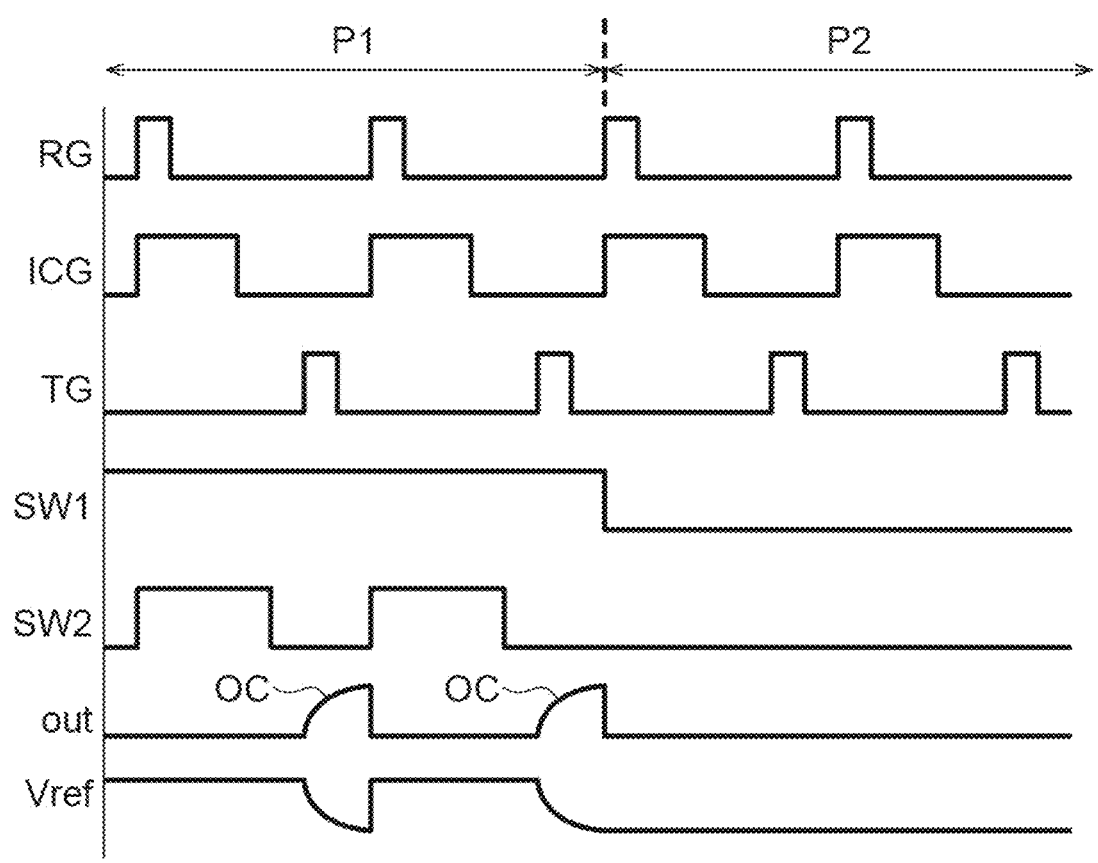
FIG. 6 is a timing chart showing an example of the operation of the smell detection device.

The operation of the adjuster 7 will be described in detail with reference to the timing chart shown in FIG. 6. Note that the timing chart shown in FIG. 6 is an example of the case where the out signal is extracted by the above-described ICG driving system. For the sake of simplicity, the gain adjuster 72 is omitted. That is, the signal output from the feedback circuit 71 is directly used as the drive signal (Vref).

The period P1 is a feedback period in which the switch SW1 is turned on to input the out signal to the feedback circuit 71, thereby adjusting the drive signal. The adjustment of the drive signal in the period P1 is performed in the standard state. In the example of FIG. 6, the out signal (output voltage) extracted by the ICG driving system includes an offset component OC (deviation in the positive direction) from the standard voltage. In the feedback circuit 71, by keeping the switch SW2 in the off state when the out signal is input, the drive signal adjusted to cancel the offset component OC of the out signal is obtained. That is, the drive signal is shifted by the same amount as the offset component OC of the out signal in a direction opposite to the offset direction of the out signal. In the example of FIG. 6, the drive signal is adjusted by two frames (two times of extraction of the out signal by the ICG driving system), but the drive signal may be adjusted by one frame or three frames or more.

The period P2 is a measurement period in which smell measurement is performed using the adjusted drive signal. Specifically, after the drive signal is adjusted, the switch SW1 and the switch SW2 are kept in the off state, so that the adjusted drive signal is maintained. That is, the adjuster 7 (feedback circuit 71) continues to output the adjusted drive signal. Thus, the offset component OC is excluded from the out signal. As a result, the standard voltage is continuously output as the out signal in the standard state. Specifically, in the present embodiment, the potential of the potential well 14 of the sensing section 10 is adjusted by adjusting the reference voltage Vref, which is a drive signal, as described above. As a result, the electric charge amount filled in the potential well 14 is adjusted so that the offset component OC of the out signal is cancelled. For example, as in the example shown in FIG. 6, when the out signal includes the offset component OC in the positive direction (the direction in which the voltage increases (=the direction in which the electric charge amount extracted from the FD portion 31 decreases)), the reference voltage Vref is adjusted to be lower by the adjuster 7. As a result, the potential of the potential well 14 rises, and the electric charge amount that is filled in the potential well 14 and extracted from the FD portion 31 is adjusted to increase. This suppresses the offset component OC of the out signal. In the example of FIG. 6, the smell substance is not detected in the period P2, and the standard state is maintained.

The smell detection device 1 described above includes an adjuster 7 that adjusts the drive signal (reference voltage Vref in the present embodiment) for driving the ion sensor 2 so as to reduce the offset of the out signal of the ion sensor 2. Therefore, as described above, the offset component OC of the out signal can be reduced by adjusting the drive signal by the adjuster 7 in the standard state, for example. The offset component OC of the out signal can be suppressed by adjusting the drive signal, which is an input signal to the ion sensor 2. Therefore, according to the smell detection device 1, it is possible to suppress a decrease in the dynamic range due to the offset component OC of the out signal. That is, the dynamic range of the output can be increased as compared with the case where the offset component OC of the out signal is removed by subsequent correction of the out signal.

The adjuster 7 is configured to be able to switch between a first operation mode in which the drive signal is adjusted based on the out signal and a second operation mode in which the drive signal adjusted in the first operation mode is maintained. In the present embodiment, the operation in the feedback period (period P1) described above (that is, the operation of keeping the switch SW1 on state and keeping the switch SW2 off state when the out signal is input to adjust the drive signal) corresponds to the first operation mode. The operation in the measurement period (period P2) described above (that is, the operation of keeping each of the switches SW1 and SW2 off state maintaining the adjusted drive signal) corresponds to the second operation mode. According to the above configuration, it is possible to appropriately switch between the first operation mode for adjusting the drive signal and the second operation mode for performing smell detection using the adjusted drive signal according to the situation. Further, in the present embodiment, the first operation mode and the second operation mode can be easily switched by the switching processing of the switches SW1 and SW2.

The smell detection device 1 includes the electrode 4 for applying a reference voltage Vref to the substance adsorption film 3, and the drive signal to be adjusted by the adjuster 7 is the reference voltage Vref. According to the above configuration, the offset component OC of the out signal can be suitably suppressed by adjusting the reference voltage Vref applied to the substance adsorption film 3.

As described above, the adjuster 7 may include the gain adjuster 72 in addition to the feedback circuit 71. According to the above-described configuration, it is possible to obtain the drive signal which is adjusted in the direction of reducing the offset of the out signal by the feedback circuit 71 and is adjusted to an appropriate magnitude by the gain adjuster 72.

The adjustment of the drive signal by the adjuster 7 may be performed collectively for all the pixels included in the ion sensor 2. For example, the adjuster 7 provided in common to all the pixels may adjust the drive signal based on a signal (for example, a signal obtained by averaging the out signals of the plurality of pixels) obtained by acquiring the out signals of the plurality of pixels and statistically processing the out signals. In this case, only one electrode 4 and only one adjuster 7 need be provided in the ion sensor 2, so that the circuit scale can be reduced.

Further, the adjustment of the drive signal by the adjuster 7 may be performed in an arbitrary pixel group unit. The pixel group is a unit having one or more pixels each having an independent sensitive film 13. In the present embodiment, as an example, a plurality of pixels (detection units 5) corresponding to the same substance adsorption film 3 form one pixel group. That is, the substance adsorption film 3 is provided for each pixel group. In the present embodiment, the ion sensor 2 has five pixel groups. In this case, the adjuster 7 is provided for each pixel group. Further, an object (here, the electrode 4) to which the drive signal output from the adjuster 7 is input is also provided for each pixel group. The adjuster 7 provided in one pixel group adjusts the drive signal common to each pixel included in the one pixel group based on the out signal of each pixel included in the one pixel group. As described above, by adjusting the drive signal for each pixel group, it is possible to individually adjust the drive signal in accordance with the characteristics of each pixel group, compared to a case where the drive signal is collectively adjusted for all the pixels included in the ion sensor 2. In particular, in the case where a plurality of (five) different substance adsorption films 3 are provided as in the present embodiment, the characteristic change caused by the above-described output drift or the like can be different for each substance adsorption film 3. Therefore, an offset component OC having a different size may be generated for each substance adsorption film 3. Therefore, it is not preferable to adjust the drive signal by the adjuster 7 common to the plurality of pixel groups. On the other hand, by adjusting the drive signal for each pixel group as described above, the drive signal can be appropriately adjusted in accordance with the characteristics of each substance adsorption film 3.

Next, the smell detection method by the smell detection device 1 will be described. First, an out signal of the ion sensor 2 is acquired in a state where the smell detection device 1 is disposed in an atmosphere in which the smell substance to be detected does not exist, and the drive signal is adjusted so that an offset from the standard voltage in the out signal is reduced (first step). That is, the processing of the first step is a processing of adjusting the drive signal as in the period P1 shown in FIG. 6 based on the out signal in the standard state described above. The method of arranging the smell detection device 1 in an atmosphere in which the smell substance is not present is not particularly limited. For example, the processing of the first step may be realized by disposing the smell detection device 1 in a closed space configured to be capable of performing both suction of air inside and introduction of any air into the inside, and introducing clean air containing no smell substance into the closed space after sucking the air in the closed space.

Subsequently, the air to be inspected is introduced into the smell detection device 1 while maintaining the drive signal adjusted in the first step (second step). In this embodiment, the operation mode of the adjuster 7 is switched from the first operation mode corresponding to the period P1 shown in FIG. 6 to the second operation mode corresponding to the period P2. As a result, the adjuster 7 continues to input the adjusted drive signal (reference voltage Vref) to the electrode 4. A method of introducing air to be inspected into the smell detection device 1 is not particularly limited. For example, air in the closed space may be sucked in a state where the smell detection device 1 is disposed in the closed space described above, and then air to be inspected may be introduced into the closed space.

Subsequently, the smell substance is detected based on the out signal of the ion sensor obtained after the second step (third step). In the present embodiment, as described above, the detector 6 detects the smell substance based on the difference (change amount) between the output value of the out signal and the standard voltage.

According to the smell detection method, it is possible to appropriately adjust the drive signal in an atmosphere in which the smell substance is not present (that is, in an environment in which the out signal of the ion sensor 2 ideally coincides with the standard voltage). Then, by performing smell detection using the adjusted drive signal, the offset component OC of the out signal can be suppressed. Therefore, according to the smell detection method, it is possible to effectively suppress a decrease in the dynamic range caused by the offset component OC of the out signal.

Further, the processing of the first step may be executed again after a predetermined period has elapsed since the processing of the second step described above was executed. Once the drive signal is adjusted, the offset component OC of the out signal gradually increases over time due to changes over time in the environment (e.g., temperature, humidity, etc.) around the ion sensor 2. According to the above configuration, by periodically adjusting the drive signal, it is possible to continuously perform smell detection in a state in which the offset component OC of the out signal is suppressed to a predetermined value or less.

Although the above embodiment has been described focusing on the case of detecting a change from a state in which the smell substance is not present to a state in which the smell substance is present, according to the smell detection method using the smell detection device 1, it is also possible to detect (observe) a state in which the smell substance decreases from the state in which the smell substance is present (state in which the smell substance is filled).

Second Embodiment

Figure 7:
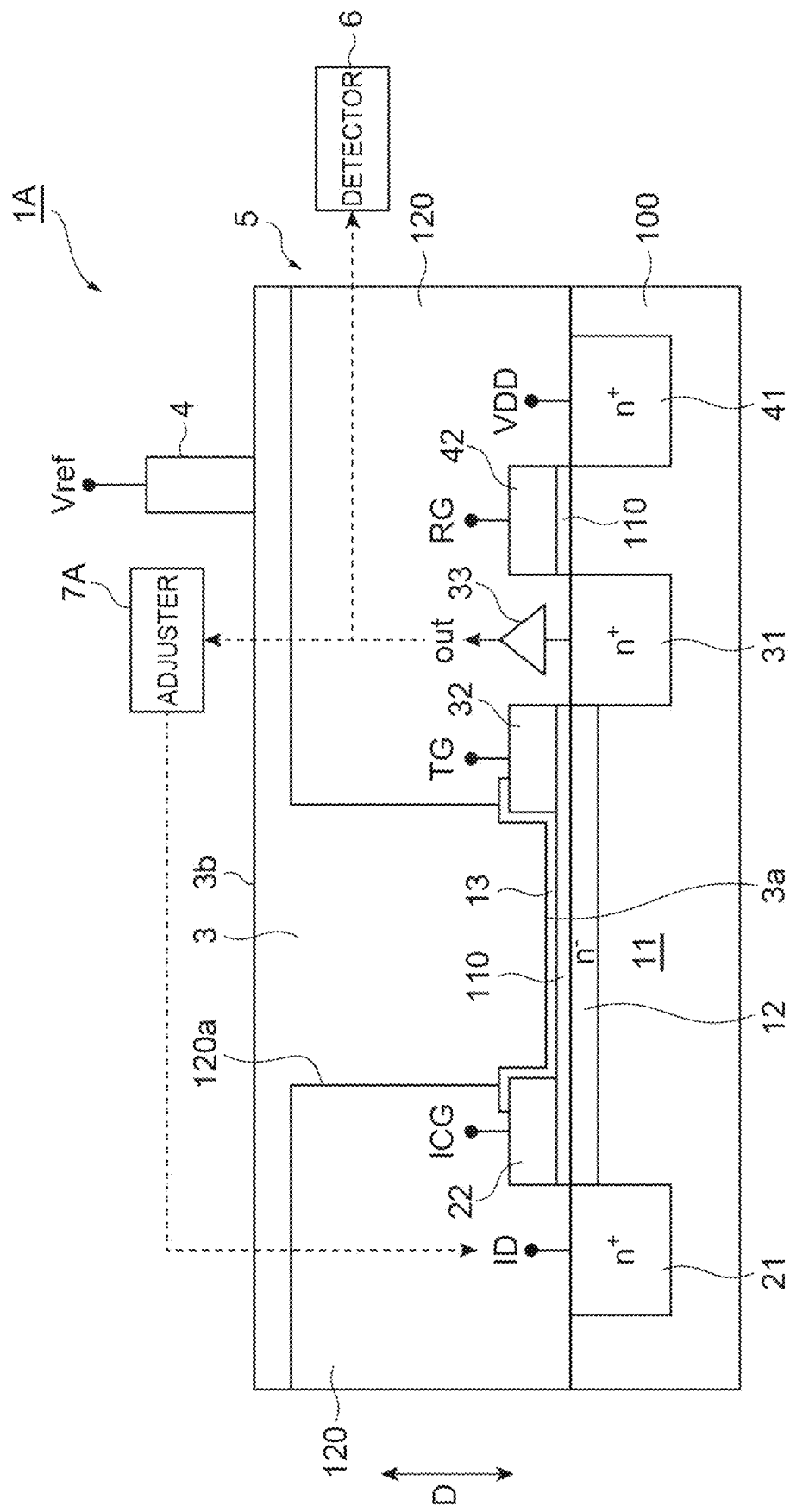
FIG. 7 is a diagram schematically showing a cross-sectional configuration of a detection unit of the smell detection device of the second embodiment.

FIG. 7 is a diagram schematically showing a cross-sectional configuration of the detection unit 5 of a smell detection device 1A of the second embodiment. In the smell detection device 1A, the ion sensor 2 is configured to operate each detection unit 5 by the above-described ICG driving system (see FIG. 4). Further, as shown in FIG. 7, the smell detection device 1A is different from the smell detection device 1 in that an adjuster 7A for adjusting the voltage applied to the ID portion 21 is provided instead of the adjuster 7 for adjusting the reference voltage Vref. That is, in the smell detection device 1A, the voltage applied to the ID portion 21 is used as the drive signal to be adjusted so that the offset of the out signal decreases.

The configuration and operation of the adjuster 7A are similar to those of FIGS. 5 and 6 in which "Vref" is replaced with "voltage applied to the ID portion 21". In the smell detection device 1A, a reference voltage Vref is input to the electrode 4 from a power supply different from the adjuster 7A.

According to the smell detection device 1A, the voltage applied to the ID portion 21 (that is, the potential of the ID portion 21) is adjusted so that the offset component OC of the out signal is cancelled. For example, as in the example shown in FIG. 6, when the out signal includes the offset component OC in the positive direction (the direction in which the voltage increases (=the direction in which the electric charge amount extracted from the FD portion 31 decreases)), the potential of the ID portion 21 is adjusted to be lower by the adjuster 7A. As a result, the electric charge amount filled in the potential well 14 and taken out from the FD portion 31 is adjusted to increase. This suppresses the offset component OC of the out signal.

According to the smell detection device 1A, in the ion sensor 2 configured to inject the electric charge into the potential well 14 by changing the potential of the ICG portion 22 while keeping the potential of the ID portion 21 constant, the offset component OC of the out signal can be suitably suppressed by adjusting the voltage of the ID portion 21 that determines the injection amount of the electric charge.

Third Embodiment

Figure 8:
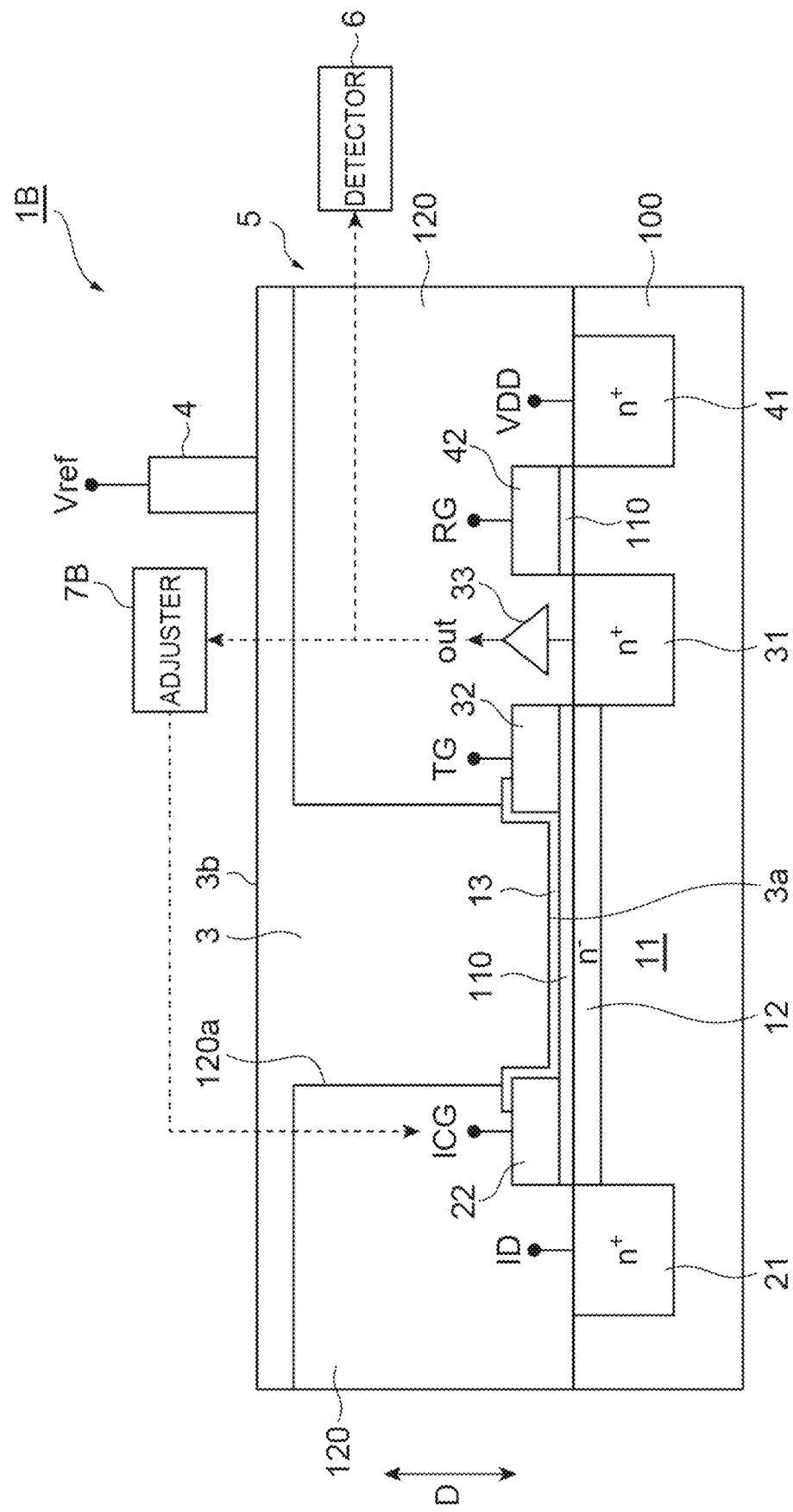
FIG. 8 is a diagram schematically showing a cross-sectional configuration of a detection unit of the smell detection device of the third embodiment.

FIG. 8 is a diagram schematically showing a cross-sectional configuration of the detection unit 5 of a smell detection device 1B of the third embodiment. In the smell detection device 1B, the ion sensor 2 is configured to operate each detection unit 5 by the above-described ID driving system (see FIG. 3). As shown in FIG. 8, the smell detection device 1B is different from the smell detection device 1 in that an adjuster 7B for adjusting the voltage applied to the ICG portion 22 is provided instead of the adjuster 7 for adjusting the reference voltage Vref. That is, in the smell detection device 1B, the voltage applied to the ICG portion 22 is used as the drive signal to be adjusted so as to reduce the offset of the out signal.

The configuration and operation of the adjuster 7B are the same as those in FIGS. 5 and 6 in which "Vref" is replaced with "voltage applied to the ICG portion 22". In the smell detection device 1B, a reference voltage Vref is input to the electrode 4 from a power supply different from the adjuster 7B.

According to the smell detection device 1B, the voltage applied to the ICG portion 22 (that is, the potential of the ICG region) is adjusted so that the offset component OC of the out signal is cancelled. For example, as in the example illustrated in FIG. 6, when the out signal includes the offset component OC in the positive direction (the direction in which the voltage increases (=the direction in which the electric charge amount extracted from the FD portion 31 decreases)), the potential of the ICG region is adjusted to be lower by the adjuster 7B. As a result, the electric charge amount filled in the potential well 14 and taken out from the FD portion 31 is adjusted to increase. This suppresses the offset component OC of the out signal.

According to the above configuration, in the ion sensor 2 configured to inject the electric charge into the potential well 14 by changing the potential of the ID portion 21 in a state where the potential of the ICG portion 22 is constant, the offset component OC of the out signal can be suitably suppressed by adjusting the voltage of the ICG portion 22 that determines the so-called leveling height of the electric charge.

Note that it takes a relatively long time to perform the slide cutting operation of the ID driving system (that is, the operations of (B) to (C) of FIG. 3). Therefore, from the viewpoint of speeding up the detection operation per one cycle as much as possible, it is preferable to adopt the first embodiment in which the reference voltage Vref is adjusted or the second embodiment in which the voltage applied to the ID portion 21 is adjusted after adopting the ICG driving system. Further, in a case where it is difficult to separate the electrode 4 for each pixel group (for example, in a case where the electrode 4 is configured as the above-described external electrode) and it is desired to adjust the drive signal for each pixel group, it is preferable to adopt the second embodiment after providing the ID portion 21 for each pixel group.

Fourth Embodiment

Figure 9:
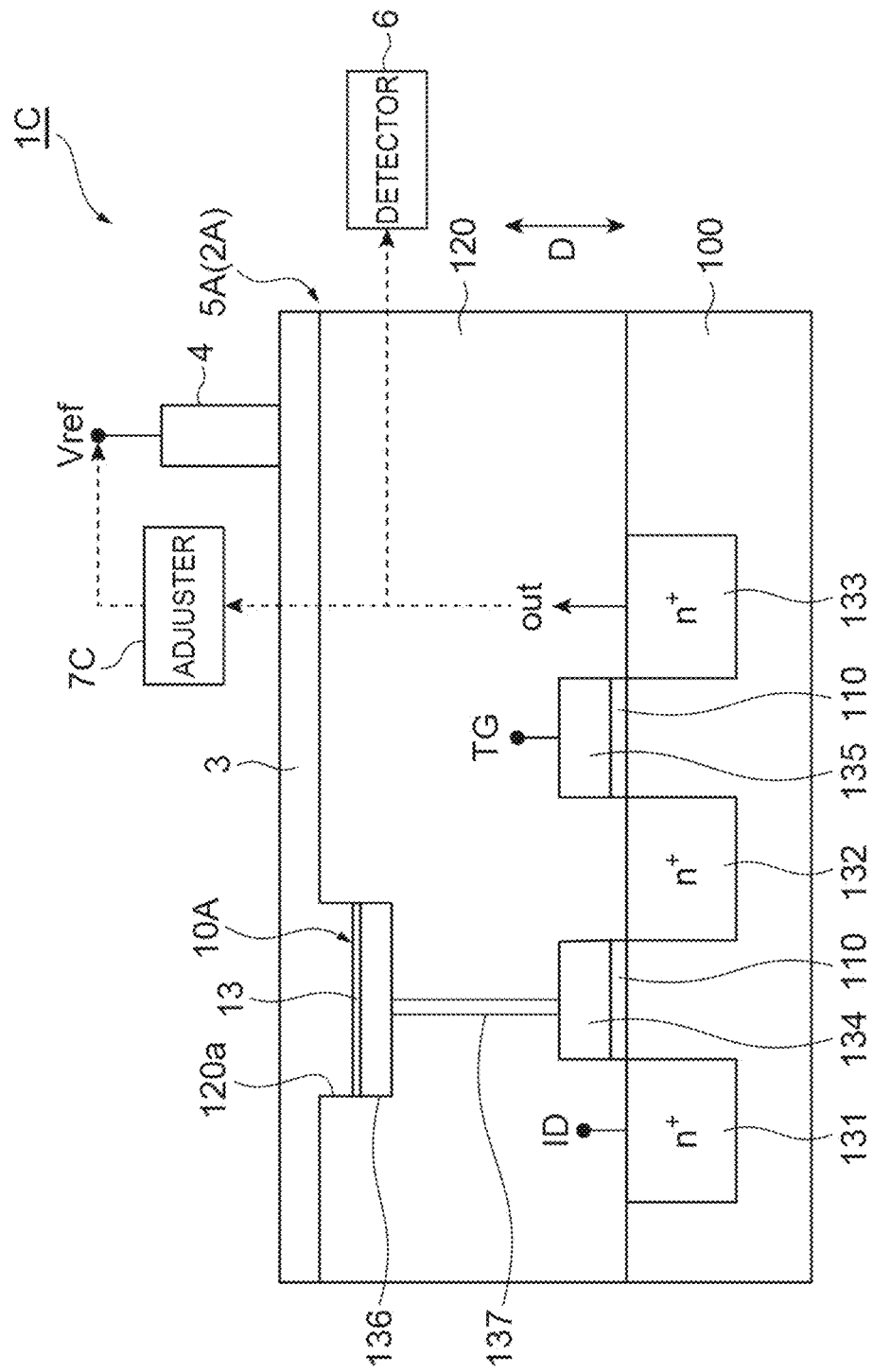
FIG. 9 is a diagram schematically showing a cross-sectional configuration of a detection unit of the smell detection device of the fourth embodiment.

FIG. 9 is a diagram schematically showing a cross-sectional configuration of a detection unit 5A of a smell detection device 1C of the fourth embodiment. The smell detection device 1C is different from the smell detection device 1 in that a so-called ISFET type ion sensor 2A is provided instead of the ion sensor 2 which is a so-called charge transfer type CMOS image sensor. Other configurations are similar to those of the smell detection device 1. The ion sensor 2A is different from the ion sensor 2 in that the detection unit 5A employing an ISFET type measurement method is provided as a unit detection element (pixel) instead of the detection unit 5 employing a charge transfer type measurement method.

In the detection unit 5A, three $n^+$ type regions 131 to 133 of the first conductivity type (here, n-type) are formed on one main surface side of the substrate 100. Two gate electrodes 134 and 135 are formed on the main surface of the substrate 100 via an insulating protective film 110. The gate electrode 134 is positioned between the $n^+$ type region 131 and the $n^+$ type region 132. The $n^+$ type region 131, the $n^+$ type region 132, and the gate electrode 134 constitute a MOS transistor. The $n^+$ type region 131 is supplied with an ID signal (voltage) from a controller (not shown). The gate electrode 135 is positioned between the $n^+$ type region 132 and the $n^+$ type region 133. The gate electrode 135 is supplied with a TG signal (voltage) from a controller (not shown). The $n^+$ type region 133 is electrically connected to the detector 6. A conductive member 136 on which the sensitive film 13 is placed is electrically connected to the gate electrode 134 through a conductive connecting member 137. A portion where the sensitive film 13 is provided on the conductive member 136 functions as a sensing section 10A. The sensing section 10A is a region where the sensitive film 13 is exposed to the outside (i.e., to the substance adsorption film 3) through an opening 120a of the passivation layer 120, which will be described later. The conductive member 136 has, for example, a rectangular shape having substantially the same size as the sensitive film 13 when viewed from the facing direction D in which the sensitive film 13 and the substance adsorption film 3 face each other. The sensitive film 13 is formed on the upper surface of the conductive member 136.

Similar to the detection unit 5 of the first embodiment, the insulating passivation layer 120 is formed on the main surface of the substrate 100 so as to cover the members provided on the main surface of the substrate 100 as described above. The substance adsorption film 3 is provided so as to cover the passivation layer 120. An opening 120a for exposing the upper surface of the sensitive film 13 to the outside is formed in the passivation layer 120. The sensitive film 13 is in contact with the substance adsorption film 3 through the opening 120a. The standard voltage is applied to the substance adsorption film 3 by the electrode 4. In the example of FIG. 9, the upper surface of the sensitive film 13 is located at a position recessed from the upper surface of the passivation layer 120 toward the substrate 100, but the sensitive film 13 may be provided such that the upper surface of the sensitive film 13 is continuous with (flatly connected to) a portion of the passivation layer 120 where the opening 120a is not formed.

Next, the operation principle of detection unit 5A will be described. When the smell substance is adsorbed to the substance adsorption film 3, the property of the substance adsorption film 3 is changed, and the membrane potential of the sensitive film 13 is changed accordingly. As a result, the potential of the gate electrode 134 electrically connected to the sensitive film 13 changes. The smell detected in the substance adsorption film 3 (i.e., the smell substance adsorbed by the substance adsorption film 3) is detected based on the difference between the output signal (out signal) corresponding to the potential change of the gate electrode 134 and the standard voltage. An example of the operation of the detection unit 5A (driving method) will be described below.

Figure 10:
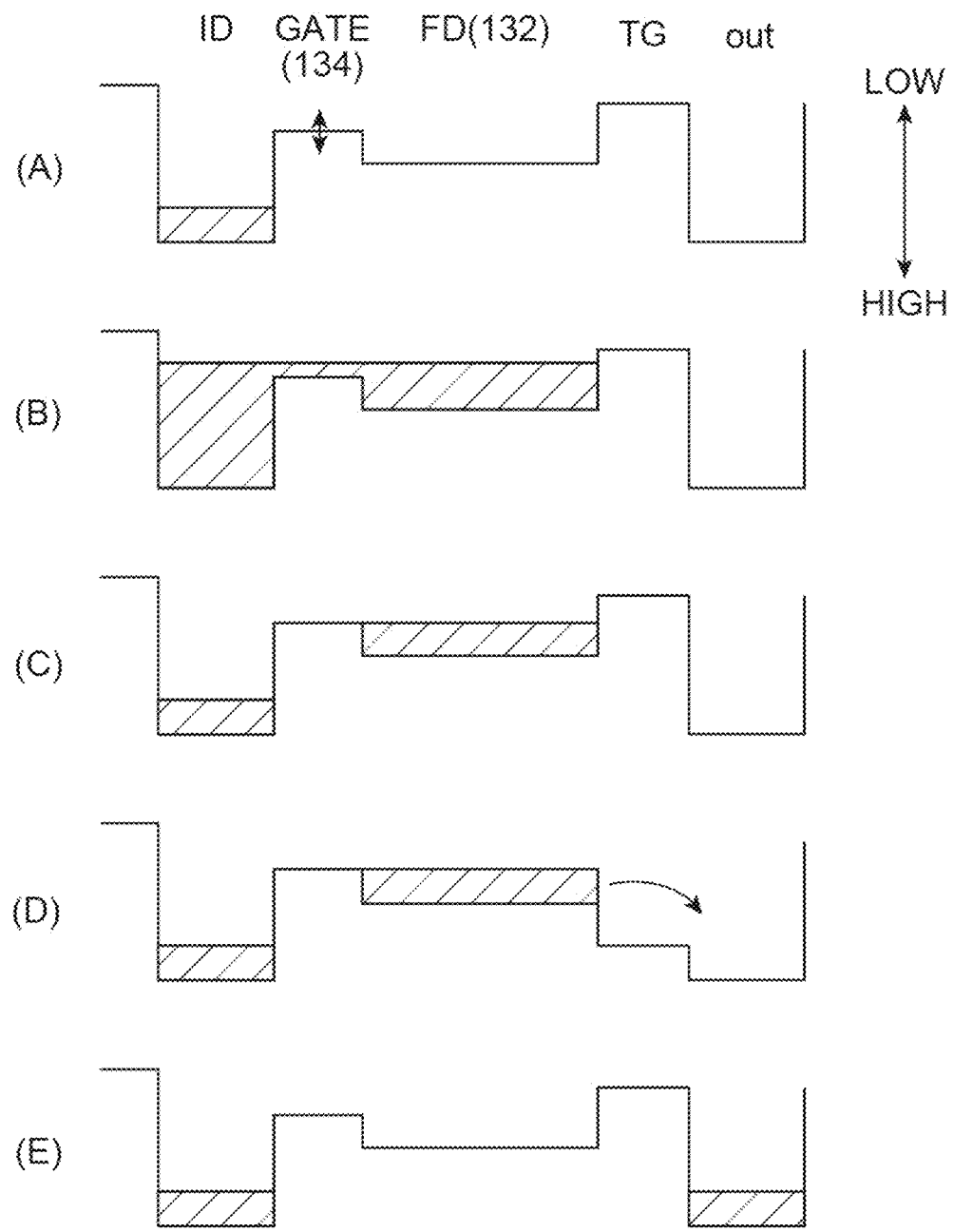
FIG. 10 is a diagram showing an example of the operation of detection unit 5A shown in FIG. 9.

In the present embodiment, as an example, the ion sensor 2A generally detects the smell by a method in which a region (hereinafter, referred to as a "gate region") facing the gate electrode 134 in the substrate 100 functions as the ICG region in the charge transfer type detection unit 5 described above, and the $n^+$ type region 132 functions as the FD portion 31 in the detection unit 5. Referring to FIG. 10, an operation example of the detection unit 5A will be described in detail. As shown in (A) of FIG. 10, the depth of the potential well of the gate region changes in accordance with the potential change of the sensitive film 13. As shown in (B) of FIG. 10, the potential of the $n^+$ type region 131 ("ID" in FIG. 10) is lowered by controlling the ID signal. Accordingly, electric charge is accumulated in the $n^+$ type region 131. The electric charge accumulated in the $n^+$ type region 131 is injected into the $n^+$ type region 132 beyond the gate region. At this time, the potential of the TG region is controlled to be lower than the potential of the $n^+$ type region 131. Therefore, the electric charge injected into the $n^+$ type region 132 does not reach the $n^+$ type region 133 ("out" in FIG. 10) beyond the TG region.

Subsequently, as shown in (C) of FIG. 10, the electric charge is extracted from the $n^+$ type region 131 by restoring (raising) the potential of the $n^+$ type region 131. As a result, the electric charge scraped off by the gate region remains in the $n^+$ type region 132. The electric charge amount left in the $n^+$ type region 132 corresponds to the depth of the potential well of the gate region.

Subsequently, as shown in (D) of FIG. 10, the voltage of the gate electrode 135 is increased, so that the electric charge remaining in the n$^+$ type region 132 is transferred to the n$^+$ type region 133. After that, the voltage of the gate electrode 135 is returned to the original voltage, so that the state shown in (E) of FIG. 10 is obtained. In this state, a signal corresponding to the electric charge amount accumulated in n$^+$ type region 133 (i.e., a signal corresponding to the potential of the sensitive film 13) is output as an out signal to the detector 6 and the adjuster 7C.

Like the adjuster 7, the adjuster 7C adjusts the reference voltage Vref (drive signal) based on the out signal. The configuration and operation of the adjuster 7C are similar to the configuration (see FIG. 5) and operation (see FIG. 6) of the adjuster 7. According to the smell detection device 1D, the reference voltage Vref, which is a drive signal, is adjusted as described above, whereby the potential of the gate region described above is adjusted. Accordingly, the electric charge amount left in the n$^+$ type region 132 is adjusted so that the offset component OC of the out signal is cancelled. For example, as in the example shown in FIG. 6, when the out signal includes an offset component OC in the positive direction (the direction in which the voltage increases (=the direction in which the electric charge amount extracted from the n$^+$ type region 132 decreases)), the reference voltage Vref is adjusted to be lower by the adjuster 7C. As a result, the potential of the gate region decreases, and the electric charge amount extracted from the n$^+$ type region 132 is adjusted to increase. This suppresses the offset component OC of the out signal.

Although the preferred embodiments of the present disclosure have been described in detail, the present disclosure is not limited to the above embodiments. For example, in the ion sensors 2A and 2B, the plurality of detection units may be arranged two-dimensionally or one dimensionally. The ion sensor may include only one detection unit. Further, the substrate 100 is not necessarily a semiconductor substrate, and may be, for example, a substrate other than a semiconductor in which a semiconductor region (e.g., a semiconductor film) is formed on a surface of the substrate.

As described above, according to the configuration of the adjuster 7 shown in FIG. 5, when the switch SW2 is in the on state, the charge accumulation of the capacitor C2 is initialized, and the feedback circuit 71 can output a voltage value corresponding to the input voltage of the amplifier A. Therefore, the output (drive signal) of the feedback circuit 71 can be adjusted by manually adjusting the input voltage of the amplifier A by turning on the switch SW2 in the adjuster 7. That is, by the switching process of the switch SW2, the adjustment (feedback adjustment) of the drive signal based on the out signal and the manual adjustment of the drive signal can be easily switched.

As described above, the adjuster 7 illustrated in FIG. 5 (and the adjusters 7A, 7B, and 7C) does not necessarily include the gain adjuster 72. For example, the gain adjuster 72 can be omitted by appropriately designing the feedback circuit 71. For example, when the capacitance of the first conductive type region 12 is represented by Csens, the capacitance of the FD portion 31 is represented by Cfd, and the gain of the amplifier 33 is represented by Gsf (see FIG. 2), the gain adjuster 72 can be omitted by setting the capacitances of the capacitor C1 and the capacitor C2 so as to satisfy the following expression (1).

$$\text{Capacitance of capacitor } C1\text{:Capacitance of capacitor } C2 = Gsf \times Csens\text{:}Cfd \quad (1)$$

Figure 11:
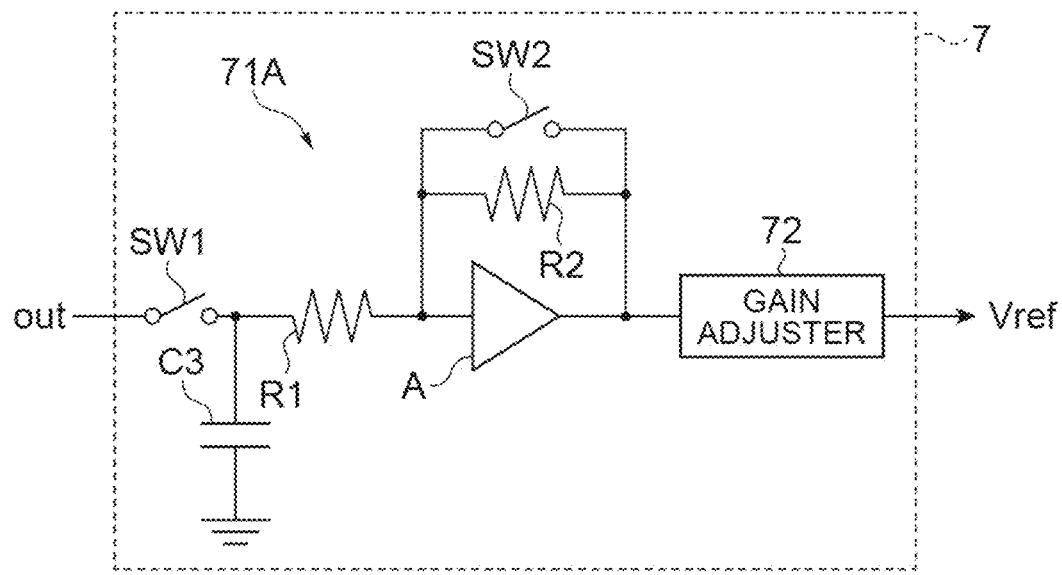
FIG. 11 is a diagram showing a modification of the adjuster.

As shown in FIG. 11, the adjuster 7 may include a feedback circuit 71A instead of the feedback circuit 71. The feedback circuit 71A includes a resistor R1 instead of the capacitor C1 and a resistor R2 instead of the capacitor C2. The feedback circuit 71A includes a hold capacitor C3 provided in parallel between the signal line input from the switch SW1 and the standard voltage. In the feedback circuit 71A, the electric charge stored in the hold capacitor C3 is converted into a voltage, and the voltage is input to an inverting amplifier circuit (a portion where the amplifier A and the resistor R2 are connected in parallel). In this case, the gain adjuster 72 can be omitted by setting the register values of the register R1 and the register R2 so as to satisfy the following expression (2).

$$\text{Registance value of register } R1\text{:Registance value of register } R2 = Gsf \times Csens\text{:}Cfd \quad (2)$$

REFERENCE SIGNS LIST 1, 1A, 1B, 1C smell detection device
2, 2A, 2B ion sensor
3 substance adsorption film
4 electrode
5, 5A detection unit (pixel)
7, 7A, 7B, 7C adjuster
13 sensitive film (ion sensitive portion)
14 potential well
21 ID portion
22 ICG portion
71 feedback circuit (first adjuster)
72 gain adjuster (second adjuster).

The invention claimed is:

1. A smell detection device comprising:
an ion sensor having an ion sensitive portion and configured to output an output signal in accordance with a potential change of the ion sensitive portion;
a substance adsorption film disposed on the ion sensitive portion and configured to change a state of the substance absorption film by adsorbing a smell substance to be detected and to cause the potential change of the ion sensitive portion; and
an adjuster configured to acquire the output signal of the ion sensor and adjust a drive signal for driving the ion sensor to reduce an offset from a predetermined reference value in the output signal,
wherein the ion sensor includes:
an ID portion configured to store an electric charge to be injected into a potential well whose depth changes in accordance with the potential change of the ion sensitive portion; and
an ICG portion configured to control an amount of the electric charge injected from the ID portion to the potential well,
wherein the ion sensor is configured to inject the electric charge from the ID portion into the potential well by changing a potential of the ID portion while keeping a potential of the ICG electrode constant, and
wherein the drive signal is a voltage applied to the ICG portion.

2. The smell detection device according to claim 1, wherein the adjuster includes:
a first adjuster configured to receive the output signal and output a signal adjusted in a direction opposite to an offset direction of the output signal; and a second adjuster configured to generate the drive signal by adjusting a gain of the signal output by the first adjuster.

3. The smell detection device according to claim 1, wherein the ion sensor includes a plurality of pixel groups, wherein each pixel group of the plurality of pixel groups includes one or more pixels each having the ion sensitive portion independently, wherein the adjuster is provided for the each pixel group, and wherein the adjuster provided in one pixel group is configured to adjust the drive signal common to each pixel included in the one pixel group based on the output signal of the each pixel included in the one pixel group.

4. The smell detection device according to claim 3, wherein the substance adsorption film is provided for the each pixel group.

5. The smell detection device according to claim 1, wherein the adjuster is configured to be able to switch between a first operation mode in which the drive signal is adjusted based on the output signal and a second operation mode in which the drive signal adjusted in the first operation mode is maintained.

6. A smell detection method by a smell detection device comprising: an ion sensor having an ion sensitive portion and configured to output an output signal in accordance with a potential change of the ion sensitive portion; and a substance adsorption film disposed on the ion sensitive portion and configured to change a state of the substance absorption film by adsorbing a smell substance to be detected and to cause the potential change of the ion sensitive portion, comprising:
- a first step of acquiring an output signal of the ion sensor and adjusting a drive signal for driving the ion sensor such that an offset from a predetermined reference value in the output signal is reduced, in a state where the smell detection device is disposed in an atmosphere in which the smell substance to be detected does not exist;
- a second step of introducing an air to be inspected into the smell detection device while maintaining the drive signal adjusted in the first step; and
- a third step of detecting the smell substance based on the output signal of the ion sensor obtained after the second step, wherein the ion sensor includes:
- an ID portion configured to store an electric charge to be injected into a potential well whose depth changes in accordance with the potential change of the ion sensitive portion; and
- an ICG portion configured to control an amount of the electric charge injected from the ID portion to the potential well, wherein the ion sensor is configured to inject the electric charge from the ID portion into the potential well by changing a potential of the ID portion while keeping a potential of the ICG electrode constant, and wherein the drive signal is a voltage applied to the ICG portion.

7. The smell detection method according to claim 6, wherein the processing of the first step is executed again after a predetermined period has elapsed since the processing of the second step was executed.

8. A smell detection device comprising:
an ion sensor having an ion sensitive portion and configured to output an output signal in accordance with a potential change of the ion sensitive portion;
a substance adsorption film disposed on the ion sensitive portion and configured to change a state of the substance absorption film by adsorbing a smell substance to be detected and to cause the potential change of the ion sensitive portion; and
an adjuster configured to acquire the output signal of the ion sensor and adjust a drive signal for driving the ion sensor to reduce an offset from a predetermined reference value in the output signal,
wherein the adjuster includes:
- a first adjuster configured to receive the output signal and output a signal adjusted in a direction opposite to an offset direction of the output signal; and
- a second adjuster configured to generate the drive signal by adjusting a gain of the signal output by the first adjuster.

9. The smell detection device according to claim 8, wherein the adjuster is configured to be able to switch between a first operation mode in which the drive signal is adjusted based on the output signal and a second operation mode in which the drive signal adjusted in the first operation mode is maintained.

10. The smell detection device according to claim 8, further comprising an electrode configured to apply a reference voltage to the substance adsorption film,
wherein the drive signal is the reference voltage.

11. The smell detection device according to claim 8, wherein the ion sensor includes:
- an ID portion configured to store an electric charge to be injected into a potential well whose depth changes in accordance with the potential change of the ion sensitive portion; and
- an ICG portion configured to control an amount of the electric charge injected from the ID portion to the potential well,
wherein the ion sensor is configured to inject the electric charge from the ID portion into the potential well by changing a potential of the ICG portion while keeping a potential of the ID portion constant, and
wherein the drive signal is a voltage applied to the ID portion.

12. The smell detection device according to claim 8, wherein the ion sensor includes a plurality of pixel groups,
wherein each pixel group of the plurality of pixel groups includes one or more pixels each having the ion sensitive portion independently,
wherein the adjuster is provided for the each pixel group, and
wherein the adjuster provided in one pixel group is configured to adjust the drive signal common to each pixel included in the one pixel group based on the output signal of the each pixel included in the one pixel group.

13. The smell detection device according to claim 12, wherein the substance adsorption film is provided for the each pixel group.

14. A smell detection method by a smell detection device comprising: an ion sensor having an ion sensitive portion and configured to output an output signal in accordance with a potential change of the ion sensitive portion; and a substance adsorption film disposed on the ion sensitive portion and configured to change a state of the substance absorption film by adsorbing a smell substance to be detected and to cause the potential change of the ion sensitive portion, comprising:
- a first step of acquiring an output signal of the ion sensor and adjusting a drive signal for driving the ion sensor such that an offset from a predetermined reference value in the output signal is reduced, in a state where the smell detection device is disposed in an atmosphere in which the smell substance to be detected does not exist;
- a second step of introducing an air to be inspected into the smell detection device while maintaining the drive signal adjusted in the first step; and
- a third step of detecting the smell substance based on the output signal of the ion sensor obtained after the second step,
- wherein the adjusting is performed by an adjuster that includes:
  - a first adjuster configured to receive the output signal and output a signal adjusted in a direction opposite to an offset direction of the output signal; and
  - a second adjuster configured to generate the drive signal by adjusting a gain of the signal output by the first adjuster.

15. The smell detection method according to claim 14, wherein the processing of the first step is executed again after a predetermined period has elapsed since the processing of the second step was executed.

* * * * *